United States Patent [19]

Hosaka et al.

[11] Patent Number: 4,656,144

[45] Date of Patent: * Apr. 7, 1987

[54] IMMUNOPARTICLES AND PROCESS FOR PREPARING SAME

[75] Inventors: Shuntaro Hosaka; Yasuo Murao, both of Kamakura, Japan

[73] Assignee: Toray Industries, Incorporated, Tokyo, Japan

[*] Notice: The portion of the term of this patent subsequent to Nov. 29, 2000 has been disclaimed.

[21] Appl. No.: 757,761

[22] Filed: Jul. 22, 1985

Related U.S. Application Data

[63] Continuation of Ser. No. 328,087, Dec. 7, 1981, abandoned.

[30] Foreign Application Priority Data

Dec. 9, 1980 [JP]  Japan .................................. 55-172563
Dec. 9, 1980 [JP]  Japan .................................. 55-172564

[51] Int. Cl.$^4$ ............................................. G01N 33/546
[52] U.S. Cl. ...................................... 436/534; 424/85; 424/88
[58] Field of Search .................... 424/79, 85, 88–92, 424/86, 87; 436/112 R, 532, 533, 534

[56] References Cited

U.S. PATENT DOCUMENTS

4,202,775  5/1980  Abe et al. .............................. 424/79
4,418,152  11/1983 Hosaka et al. ........................ 436/534

OTHER PUBLICATIONS

Chemical Abstracts, vol. 95, Abstract No. 169784f, 1981.
Chemical Abstracts, vol. 92, Abstract No. 106870g, 1980.
Chemical Abstracts, vol. 95, Abstract No. 2666g, 1981.
Chemical Abstracts, vol. 92, Abstract No. 2845, 1980.
Chemical Abstracts, vol. 97, Abstract No. 123460k, 1982.

*Primary Examiner*—Blondel Hazel
*Attorney, Agent, or Firm*—Scully, Scott, Murphy & Presser

[57] ABSTRACT

Immunochemicals having an amino group are immobilized by covalent bonding on fine particles having an average diameter of 0.03 to 10 µm, the fine particles comprising a polymer having the repeating unit of glycidyl acrylate or glycidyl methacrylate and the fine particles not having on the surface thereof a hydrophobic component other than the above unit, whereby there are obtained immunoparticles effective as a diagnostic reagent for immunological tests for detecting or measuring a component in human or animal body fluids or for labeling cells.

5 Claims, No Drawings

IMMUNOPARTICLES AND PROCESS FOR PREPARING SAME

This application is a continuation of application Ser. No. 328,087, filed Dec. 7, 1981, now abandoned.

BACKGROUND OF THE INVENTION

The present invention relates to immunoparticles effective as diagnostic reagents for immunological tests and a process for preparing the same. More particularly, it is concerned with improved immunoparticles prepared by immobilizing immunochemicals on a particulate carrier, effective as diagnostic reagents for immunological tests for detecting or measuring a component in human or animal body fluids or for labeling cells.

In immunologically detecting or quantitatively analyzing either an antigen or antibody using the reaction between the antigen and antibody, it is an important method in immunological tests in clinical laboratories to immobilize a substance reactive with a second substance to be detected on a particulate carrier and to conduct a high sensitivity measurement by utilizing the phenomenon of agglutination which the above immobilized substance-carrier combination particles undergo in the presence of the substance to be detected. Also used widely in clinical laboratory tests is the method of immobilizing a substance to be detected on a particulate carrier, then utilizing the fact that agglutination of particles immobilizing the substance to be detected due to the presence of an antigen or antibody which specifically reacts with the substance to be detected is inhibited by the presence of the substance to be measured in the body fluids, and thereby detecting or quantitatively analyzing the substance to be detected. Moreover, the method of immobilizing a substance, which selectively binds to specific cells, on a particulate carrier and labeling the cells by determining whether or not the particles bind to the cells, has frequently been used for immunological testing.

Such immobilized immunochemicala-particulate carrier combinations are referred to as "immunoparticles".

As a particulate carrier as a part of a diagnostic reagent for immunological tests using such immunoparticles for agglutination reaction, substances used include red corpuscles of mammals or birds, particles of inorganic substances such as kaolin and carbon, and latex of organic high polymers such as natural rubber latex and polystyrene latex. Of these, red corpuscles can immobilize many kinds of antigens and antibodies and the applicable range thereof is the broadest. However, red corpuscles involve problems such that they differ in quality depending upon the individual animals from which they are drawn, are difficult to store because of insufficient stability and are sometimes non-specifically agglutinated by human serum.

It is polystyrene particles that are used most widely as non-organism originating carrier particles. Polystyrene is stable and because it is a synthetic polymer, the quality can be controlled. Because polystyrene is hydrophobic and has a property of adsorbing various proteins, immobilization of an antigen or antibody on polystyrene usually is carried out by physical adsorption. When an antigen or antibody is immobilized by physical adsorption, an equilibrium may occur between the immobilized antigen (or antibody) and a free antigen (or antibody) and result in a competitive reaction which takes place between the antigen (or antibody) immobilized on particles and the free antigen (or antibody) toward a corresponding antibody (or antigen) which is an objective substance of the measurement. This competitive reaction works to inhibit agglutination. As a result, there occur insufficient sensitivity and stability in many instances. Moreover, as a matter of course, substances difficult to be physically adsorbed to polystyrene cannot be immobilized by this method. Because of these problems, the practical application of polystyrene particles is limited as compared with red corpuscles as a carrier.

With a view to solving the aforesaid problems, it has recently been proposed to use other reagents prepared by bonding an antigen or antibody to a carrier by covalent bonding, such as reagents (see DT 2,649,218) prepared by bonding human chorionic gonadtropin to a styrene - methacrylic acid copolymer latex by using carbodiimide; reagents (see Japanese Patent Publication No. 12966/1978) comprising particles 0.01 to 0.9 microns in diameter prepared by condensing human chorionic gonadtropin, human serum albumin or denatured $\gamma$-globulin, via amide bond and using carbodiimide as a condensing agent, to various latices such as carboxylated styrene -butadiene copolymer, carboxylated polystyrene, carboxylated polystyrene having an amino group, acrylic acid polymer, acrylonitrile polymer, methacrylic acid polymer, acrylonitrile - butadiene styrene terpolymer, polyvinyl acetate acrylate, polyvinyl pyridine and vinyl chloride - acrylate copolymer; reagents [see "The Japanese Journal of Clinical Pathology", 27, Supplementary Edition, page 522 (1978)]prepared by copolymerizing methacrylic acid, 2-hydroxyethyl methacrylate and methyl methacrylate and bonding treponema antigen to a latex of the resulting copolymer containing hydroxyl group and carboxyl group by the cyanogen bromide or carbodiimide method; and reagents (see Japanese Patent Laid Open No. 110118/1980) prepared by coating polystyrene particles as a core with styrene - glycidyl methacrylate copolymer and reacting human chorionic gonadtropin or insulin with an epoxy group in the latex thereby bonding it to the latex. Many of these prior art methods use carbodiimide for bonding immunochemicals to carrier particles. But the use of carbodiimide would cause an inter- or intra-molecular condensation reaction of the immunochemicals, but in this case it is difficult to obtain the reproducibility of reaction between hydroxyl group-containing polymer and cyanogen bromide. As a result, the immunoactivity of particles with immunochemicals immobilized thereon lacks in reproducibility. As compared with these immunochemicals immobilizing methods, the method of reacting proteins or polypeptides with an epoxy group introduced in polymer causes less deterioration of immunoactivity and is superior in the reproducibility of the reaction. In the abovementioned prior art using an epoxy group, however, proteins tend to be adsorbed non-specifically because on the surfaces of the polymer particles there exists a portion originating from styrene. Generally, in human or animal body fluids there are contained various kinds of proteins, and particularly in blood plasma and serum there are contained those proteins at high concentrations. When protein is adsorbed onto carrier particles from the test body fluids, it may interfere with the objective antigen-antibody reaction and cause a reduction in the selectivity or sensitivity of the agglutination reaction.

DESCRIPTION OF THE INVENTION

It is an object of the present invention to overcome the foregoing disadvantages associated with the foregoing prior art methods.

It is another object of the present invention to provide novel immunoparticles which are effective as diagnostic reagents for immunological tests and which are stable and unlikely to agglutinate non-specifically by test body fluid and further which are free from non-specific adsorption of protein in the test body fluid and non-specific adhesion to cells, and also provide a process for preparing such novel immunoparticles.

Other objects and advantages of the present invention will become apparent from the following description.

The above-mentioned objects of the present invention are attainable by immunoparticles prepared by immobilizing, by covalent bonding, immunochemicals containing an amino group onto fine particles having an average diameter of 0.03 to 10 μm which fine particles comprise a polymer having the repeating unit of glycidyl acrylate and/or glycidyl methacrylate and which fine particles do not substantially have on the surface thereof a hydrophobic component other than the above unit.

The immunoparticles of the present invention exhibit a remarkable usefulness as a diagnostic reagent for immunological tests. According to the present invention, the immunochemicals are immobilized on the particulate carrier by covalent bonding caused by the reaction between the amino group of the immunochemicals and an epoxy group on the particle surface. In case there is the possibility that the epoxy group will not totally be consumed but remain active in its reaction with the immunochemicals, hydrophilic proteins which do not interfere with the objective immunological tests, such as serum albumin and gelatin, may be reacted with the remaining epoxy group, whereby the epoxy group is made no longer reactive. In this case, such hydrophilic proteins may be mixed and reacted together with the immunochemicals to be immobilized, or the immunochemicals may be reacted alone in advance and thereafter the hydrophilic proteins may be reacted. The above-mentioned hydrophilic proteins such as serum albumin and gelatin may be substituted by amino acids such as glycine and alanine.

According to the present invention, the fine particles before reaction with immunocchemicals, that is, the particulate carrier, may be prepared by polymerizing a mixture of addition polymerizable monomers containing as essential component(s) glycidyl acrylate and/or glycidyl methacrylate. Either glycidyl acrylate or glycidyl methacrylate may be used, or both may be used as a mixture in any desired mixing ratio.

In the preparation of the particulate carrier, addition of other comonomers often affords desirable results, particularly in the adjustment of the particle size. Hydrophilic and particularly water-soluble comonomers are desirable. Suitable examples of such water-soluble comonomers are 2-hydroxyethyl acrylate, 2-hydroxyethyl methacrylate, 2-hydroxypropyl acrylate, 2-hydroxypropyl methacrylate, the acrylic or methacrylic acid ester of polyethyleneglycol monoalkylether having a degree of polymerization ranging from 2 to 25, acrylamide, methacrylamide, N-vinylpyrrolidone and glycerol methacrylate. Two or more of these water-soluble comonomers may be used in combination. After copolymerization of these water-soluble comonomers and after immobilization of immunochemicals, it is a hydrophilic portion based on the water-soluble comonomers that is exposed on the polymer particle surface without being covered with any bonded substance. Since proteins are difficult to be adsorbed to hydrophilic polymers in an aqueous medium, the fine particles immobilizing immunochemicals according to the present invention are stable and unlikely to agglutinate non-specifically by test body fluid and are free from non-specific adhesion to cells. The molar ratio of the sum of glycidyl acrylate and glycidyl methacrylate to the sum of comonomers may be changed in the range of from 100:0 to 5:95. The epoxy group can react not only with amino group but also with carboxyl, alcoholic hydroxyl, phenolic hydroxyl and mercapto groups. By suitably selecting the manufacturing conditions for the polymer particles, the epoxy group of glycidyl acrylate or glycidyl methacrylate can be utilized in the immobilization of immunochemicals without losing it by side reaction.

The polymer particles of the present invention can be prepared by the following method.

The polymerization reaction usually is carried out by emulsion polymerization, precipitation polymerization or suspension polymerization. Any of these polymerization methods is suitable for the purpose of the present invention because the polymer is produced as particles during the polymerization reaction. Particularly preferred is the precipitation polymerization which is carried out in a medium which dissolves the monomer or monomers but does not dissolve the polymer produced. In the precipitation polymerization method, by suitably selecting the combination of the monomer or monomers and the polymerization medium it becomes relatively easy to adjust the average diameter of the polymer particles produced within the range of from 0.03 to 10 μm, and the particle size distribution is relatively narrow. Unlike emulsion polymerization and suspension polymerization, the precipitation polymerization does not require the use of an emulsifier or a suspension stabilizer, so it is not necessary to remove these additives after the polymerization reaction. This is one of the advantages of the precipitation polymerization method.

Examples of media which may be used in the precipitation polymerization include ethyl acetate, n-propyl acetate, isopropyl acetate, butyl acetate and their isomers, and the propionic acid esters corresponding to the foregoing, ketones such as methyl ethyl ketone, methyl n-propyl ketone, methyl isopropyl ketone, methyl butyl ketone and their isomers, as well as benzene, toluene, o-xylene, m-xylene, p-xylene, and carbon tetrachloride.

Although the addition of a cross-linking agent to the polymerization system is not essential, it is usually desirable to add upon polymerization a polyfunctional monomer containing two or more polymerizable carbon-carbon double bonds in the molecule to thereby cross link the polymer. There are many polyfunctional monomers suitable for addition to the polymerization system for such purpose, examples of which include divinyl benzene, ethyleneglycol dimethacrylate, N,N'-methylenebisacrylamide, divinyl succinate, diallyl succinate, vinyl methacrylate, allyl methacrylate, triallyl cyanurate, and triallyl isocyanurate. The amount of the cross-linking agent to be added usually is not more than 30 mol % of the total monomers. The cross-linking may be introduced by utilizing the reactivity of the produced polymer after the polymerization reaction, that is, by reacting the produced polymer with a polyfunctional compound. For example, the polymer may be cross-linked by reacting epoxy groups contained in the produced polymer with a diamine such as ethylene diamine.

As the polymerization initiator there may be used conventional radical polymerization initiators, for example, azo compounds such as 2,2'-azobisisobutyronitrile, 2,2'-azobis(2,4-dimethylvaleronitrile) and 2,2'-azobis(2,4-dimehyl-4-methoxyvaleronitrile), and peroxides such as benzoyl peroxide, dilauroyl peroxide and ditertiary-butyl peroxide.

The polymerization temperature may be within the temperature range of an ordinary radical polymerization. The range of 20°-80° C. is particularly preferred.

The concentration of the polymerization initiator in the polymerization mixture of the present invention is about 0.001-0.03 mol/liter. The concentration of the monomer in the polymerization mixture is preferably within the range of 5-50% by weight. If the monomer concentration exceeds 50% by weight, the resulting polymer particles tend to coagulate. At monomer concentrations less than 5% by weight, the present invention can be practiced, but the productivity decreases because the yield of the resulting polymer particles becomes smaller. It is preferable that the polymerization be carried out after replacing the air with an inert gas such as nitrogen or argon.

The shape of the particles produced is spherical in many cases, but the spherical shape is not always required and the particles may take irregular shapes. The diameter of an irregularly shaped particle is defined as 1/2 of the sum of the largest diameter and the smallest diameter. The average diameter is expressed by $\bar{d}$ which is defined by the following formula (1):

$$\bar{d} = \sum_{i=1}^{N} d_i/N \quad (1)$$

wherein $d_i$ is the diameter of number i particle and N is a total number of particles. Experientially, it is when the average particle diameter ranges between 0.1 μm and 10 μm that the agglutination reaction is easily observable. For the purpose of labeling cells, the average particle diameter preferably ranges between 0.03 μm and 5 μm. Particles properly colored with a dye or pigment are convenient for both purposes of agglutination reaction and labeling cells. Also, particles imparted with fluorescence are preferable for labeling cells.

The immobilization reaction of immunochemicals on fine particles is carried out in an aqueous medium at a pH value ranging suitably from 7.0 to 9.0 and at a temperature ranging suitably from 0° to 40° C. The concentration of immunochemicals in the reaction solution cannot be defined by a certain specific value because it should be increased or decreased according to the properties of each individual immunochemical. As previously noted, addition of hydrophilic proteins such as serum albumin and gelatin into the reaction solution is often effective in improving the dispersion stability of the fine particles immobilizing the immunochemicals. Also, treating the reaction product with amino acids such as glycine and alanine after the immobilization reaction often affords preferable results.

Furthermore, treating the polymer particles with tannic acid before reaction thereof with immunochemicals also affords preferable results. In this case, suitable range of the tannic acid concentration is 0.0001-0.1%.

It is necessary that the immunochemicals used in the invention should contain an amino group. But this condition is satisfied in most cases because most of immunochemicals are either protein or contain peptide moiety. The immunochemicals as referred to herein mean not only antigens and antibodies but also substances which participate in liquid or cellular immunological reactions and bond specifically to certain substances, such as complement, Fc receptor and $C_3$ receptor. Examples thereof include Treponema pallidum antigen, hepatitis B surface antigen (HBs antigen), anti-HBs antigen antibody, rubella viral antigen, toxoplasma antigen, streptolysin O, anti-streptolysin O antibody, mycoplasma antigen, human chorionic gonadtropin (HCG), anti-HCG antibody, aggregated human IgG, rheumatoid factor, nuclear protein, DNA, anti-DNA antibody, C-reactive protein (CRP), anti-CRP antibody, anti-estrogen antibody, $\alpha$-fetoprotein ($\alpha$-FP), anti-$\alpha$-FP antibody, carcinoembryonic antigen (CEA), anti-CEA antibody, Clq, anti-Clq antibody, C3, anti-C3 antibody, anti C3b antibody, anti-C3bi antibody, C4, anti-C4 antibody, protein-A, conglutinin, and immunoconglutinin.

The fine particles of the present invention are characterized in that they are stable to test body fluids; they are unlikely to be agglutinated non-specifically by such fluids; they do not non-specifically adsorb protein of the test body fluids; they may be used successfully for detecting or measuring an immunological reaction by agglutination of particles; they are free from non-specific adhesion to cells; and they may be successfully used in labeling cells.

The present invention is further described by, but not limited to, the examples which follows.

EXAMPLE 1

Glycidyl methacrylate, 2-hydroxyethyl methacrylate and ethyleneglycol dimethacrylate were mixed at a molar ratio of 85.7:9.5:4.8. Then, a mixture comprising 24 parts (by weight, as will also apply hereinafter) of the resultant monomer mixture, 76 parts of ethyl propionate and 0.13 part (4.7 mmol/liter) of 2,2'-azobis(2,4-dimethyl-4-methoxyvaleronitrile) was polymerized for 3 hours at 40° C. in a nitrogen gas atmosphere. Thereafter, a whitely turbid polymerization mixture was poured into acetone and centrifuged at 1500 g for 10 minutes. The sedimental particles were dispersed again in ethanol, washed and then centrifuged again, followed by drying under reduced pressure to yield 11.3 parts of a fine particulate polymer. This polymer particles were spherical and their diameters were in the range of between 1.8 μm and 4.2 μm. The average diameter and the standard deviation were 3.3 μm and 0.45 μm, respectively.

On the polymer particles thus prepared there was immobilized TP antigen in the following manner. First, Treponema pallidum (hereinafter referred to as TP) Nichols strain was dispersed, at a ratio of $10^9$ cell/ml, in a phosphate buffered physiological saline solution (hereinafter referred to as PBS) wherein the concentration of a mixture of disodium hydrogenphosphate+potassium hydrogenphosphate was 0.01 mol/liter, the concentration of sodium chloride was 0.14 mol/liter and the pH was 7.2. The resultant dispersion was treated for 20 hours with an ultrasonic wave of 10 kHz while being cooled with ice water to destroy the cells to thereby prepare a TP antigen solution. One part by volume of the TP antigen solution and 3 parts by volume of a solution of bovine serum glycoprotein dissolved in PBS at a concentration of 1 mg/ml, were mixed and 1 ml of the resultant mixed solution was further mixed with a dispersion of 50 mg of the foregoing polymer particles in 1 ml of PBS, followed by stirring for 2 hours at 30° C. The particles were then subjected to centrifugal sedimentation in PBS 4 times and washed. The washed particles were dispersed in 20 ml of PBS containing 1% of bovine serum albumin (hereinafter referred to as BSA). This dispersion of the fine particles immobilizing the TP antigen was stored in a refrigerator at 4° C. for 3 days and then checked for activity in the following manner.

In a micro-titer plate having a U-shaped well made of polystyrene there was placed 50 μl each of a diluted syphilis positive serum having a TPHA titer of 640, which serum specimen was diluted serially to $2^n$ times starting from 10 times. As the diluent there was used a solution comprising PBS, 1% of BSA, 5% of a Reiter antigen solution "KW" for syphilic complement fixation (manufactured by Nippon Toketsu Kanso, Inc. of Japan) and 0.73 mol/liter of ammonium chloride. As a control, also with respect to syphilis negative serum there was placed the similarly diluted solution in the micro-titer plate. Then, in each well of the micro-titer plate containing the diluted serum solution there was added 50 μl each of a dispersion of fine particles immobilizing the TP antigen. After shaking for 3 minutes to mix the both, the resultant mixed solution was allowed to stand for 2 hours at room temperature, and the degree of agglutination was determined from the pattern of sedimentation. The results are as shown in Table 1, from which it is seen that the anti-TP antibody in the serum can be detected at a concentration higher than TPHA.

TABLE 1

| Dilution Ratio | 10 | 20 | 40 | 80 | 160 | 320 | 640 | 1280 | 2560 |
|---|---|---|---|---|---|---|---|---|---|
| Positive serum | +++ | +++ | +++ | +++ | +++ | +++ | ++ | ++ | + |
| Negative serum | − | − | − | − | − | − | − | − | − |

−: A small clear-cut ring at the center of the bottom
+: A ring smaller than ++
++: Small film-like (ring forming) sedimentation
+++: Film-like sedimentation throughout the bottom

EXAMPLE 2

0.4 ml of a human IgG/PBS solution having a concentration of 1 mg/ml and 1.6 ml of a bovine serum glycoprotein/PBS solution having a concentration of 1 mg/ml were mixed, and 50 mg of the same polymer particles as that used in Example 1 was dispersed in the resultant mixed solution, followed by stirring for 3 hours at 30° C. The reaction mixture was allowed to stand overnight in a refrigerator at 4° C. and then the polymer particles were washed with PBS by centrifugal sedimentation. The fine particles were dispersed again in 4 ml of PBS containing 1% of BSA and the so-prepared sispension was stirred for 2 hours at 30° C., then stored overnight in a refrigerator at 4° C. The polymer particles thus immobilizing human IgG and anti-human IgG antibody were reacted in the following manner. 10 μl of a PBS solution of an IgG fraction of anti-human IgG anti-serum (goat) and 10 μl of the above dispersion of the fine particles immobilizing human IgG were mixed on a microscopic slide glass, and the state of agglutination after 3 minutes was visually observed, the results of which are as shown in Table 2. On the other hand, a control experiment was made using an IgG fraction of a healthy goat serum not immuned with human IgG in place of the IgG fraction of anti-human IgG anti-serum (goat), in which experiment there did not occur agglutination at any of the IgG concentrations shown in Table 2. It is seen that the limit of detection of anti human IgG antibody is at its concentration of about 10 μg/ml.

TABLE 2

| Concentration of anti-human IgG antibody (μg/ml) | 10,000 | 1,000 | 100 | 10 | 1 | 0.1 |
|---|---|---|---|---|---|---|
| Agglutination | +++ | ++ | ++ | + | ± | − |

EXAMPLE 3

50 mg of the same polymer particles as that used in Example 1 were dispersed in 2 ml of a BSA/PBS solution having a concentration of 5 mg/ml and the dispersion was stirred for 7 hours at 30° C., followed by standing overnight in a refrigerator held at 4° C. After subsequent washing with PBS by centrifugal sedimentation, the polymer particles were again dispersed in 4 ml of PBS containing 0.5% of human serum albumin and the dispersion was stirred for 1 hour at 30° C., then stored in a refrigerator at 4° C. The polymer particles thus immobilizing BSA and anti-BSA anti-serum (rabbit) were reacted on the slide glass in the same manner as in Example 2, the results of which are as shown in Table 3. On the other hand, a control experiment was made using a healthy rabbit serum not immuned with BSA in place of the anti-serum shown in Table 3, in which experiment there did not occur agglutination. It is seen that the limit of detection of anti-BSA antibody is at its concentration of 0.1 μg/ml.

TABLE 3

| Concentration of anti-BSA antibody (μg/ml) | 10 | 1 | 0.1 | 0.01 |
|---|---|---|---|---|
| Agglutination | +++ | ++ | + | − |

EXAMPLE 4

Polymerization was carried out in just the same manner as in Example 1 except that the molar ratio of glycidyl methacrylate, 2-hydroxyethyl methacrylate and ethyleneglycol dimethacrylated was changed to 71.4:23.8:4.8, to obtain 10.8 parts of fine particles having an average diameter of 1.0 μm. Using the polymer particles thus obtained. BSA was immobilized in just the same manner as in Example 3. The polymer particles thus immobilizing BSA was reacted with anti-BSA anti-serum on the slide glass in the same way as in Example 3. The results were just the same as in Example 3, and the limit of detection of anti-BSA antibody was at its concentration of 0.1 μg/ml.

EXAMPLE 5

Glycidyl methacrylate, 2-hydroxypropyl methacrylate and triethyleneglycol dimethacrylate were mixed at a molar ratio of 47.6:47.6:4.8. Then, a mixture comprising 24 parts of the resulting monomer mixture, 76 parts of methyl n-propyl ketone and 0.13 part (4.7 mmol/liter) of 2,2'-azobis(2,4-dimethyl-4methoxyvaleronitrile) was polymerized for 3 hours at 40° C. in an argon atmosphere. Thereafter, a whitely turbid polymerization mixture was treated in the same manner as in Example 1 to obtain 8.4 parts of polymer particles having an average diameter of 2.5 μm. BSA was immobilized on the so-prepared polymer particles in the same manner as in Example 3, then the polymer particles were dispersed in a 0.5% aqueous human serum albumin solution so as to give a 1.25% polymer content and then reacted with anti-BSA anti-serum on the slide glass in the same way as in Example 3, the results of which are as shown in Table 4.

TABLE 4

| Concentration of anti-BSA antibody (μg/ml) | 10 | 1 | 0.1 |
|---|---|---|---|
| Agglutination | + | ± | − |

EXAMPLE 6

Polymerization was carried out in the same manner as in Example 5 except that the glycidyl methacrylate and 2-hydroxypropyl methacrylate were substituted by glycidyl acrylate and 2-hydroxyethyl methacrylate, respectively, and that the molar ratio of glycidyl acrylate, 2-hydroxyethyl methacrylate and triethyleneglycol dimethacrylate was changed to 23.8:71.4:4.8, to obtain 7.2 parts of polymer particles having an average diameter of about 1 μm. After immobilizing BSA on the so-prepared polymer particles in the same way as in Example 5, the polymer particles thus immobilizing BSA were reacted with anti-BSA anti-serum in the same way as in Example 5. The results obtained were the same as in Example 5, and the detection sensitivity of anti-BSA antibody was about 10 μg/ml.

EXAMPLE 7

Polymerization was carried out in just the same manner as in Example 1 except that the 2-hydroxyethyl methacrylate was substituted by 2-hydroxyethyl acrylate, to yield 9.5 parts of polymer particles having an average diameter of about 3 μm. Then, in the same way as in Example 1, TP antigen was immobilized on the so-prepared polymer particles and the activity of the polymer particles thus immobilizing TP antigen was verified. As a result, the detection sensitivity of syphilis antibody was the same as in Example 1.

What is claimed is:

1. A process for preparing immunoparticles, comprising polymerizing at least one monomer selected from the group consisting of glycidyl acrylate and glycidyl methacrylate in a medium in which said monomer is soluble but in which the polymer produced is not soluble, said medium being selected from the group consisting of ethyl acetate, n-propyl acetate, isopropyl acetate, butyl acetates, ethyl propionate, n-propyl propionate, isopropyl propionate, butyl propionates, methyl ethyl ketone, methyl n-propyl ketone, methyl isopropyl ketone, methyl butyl ketones, benzene, toluene, o-xylene, m-xylene, p-xylene and carbon tetrachloride, thereby precipitating a fine particulate polymer having an average particle diameter in the range of from 0.03 to 10 μm, and then reacting said fine particulate polymer with an immunochemical having an amino group.

2. A process according to claim 1, wherein said monomer is polymerized in the presence of a water-soluble monomer having an unsaturated carbon-carbon double bond.

3. A process according to claim 1, wherein said monomer is polymerized in the presence of a water-soluble monomer having an unsaturated carbon-carbon double bond and a cross-linking agent and a polymerization initiator.

4. A process according to claim 1, wherein either simultaneously with or after the reaction of said fine particulate polymer with said immunochemical, said fine particulate polymer is reacted with a hydrophilic protein.

5. A process according to claim 1, wherein before the reaction of said fine particulate polymer with said immunochemical, said fine particulate polymer is treated with tannic acid.

* * * * *